United States Patent
Hozumi

(10) Patent No.: US 10,077,510 B2
(45) Date of Patent: Sep. 18, 2018

(54) GAUZE FABRIC

(71) Applicant: UCHINO CO., LTD., Chuo-ku (JP)

(72) Inventor: Shuichi Hozumi, Chuo-ku (JP)

(73) Assignee: UCHINO CO., LTD., Chuo-ku (JP)

( * ) Notice: Subject to any disclaimer, the term of this patent is extended or adjusted under 35 U.S.C. 154(b) by 0 days.

(21) Appl. No.: 14/912,644

(22) PCT Filed: Dec. 25, 2013

(86) PCT No.: PCT/JP2013/084666
§ 371 (c)(1),
(2) Date: Feb. 18, 2016

(87) PCT Pub. No.: WO2015/097784
PCT Pub. Date: Jul. 2, 2015

(65) Prior Publication Data
US 2016/0201233 A1   Jul. 14, 2016

(51) Int. Cl.
*D03D 19/00* (2006.01)
*D03D 11/00* (2006.01)
(Continued)

(52) U.S. Cl.
CPC ........ *D03D 11/00* (2013.01); *A61F 13/00021* (2013.01); *B32B 5/024* (2013.01); *B32B 5/06* (2013.01); *B32B 5/26* (2013.01); *D03D 15/00* (2013.01); *D03D 19/00* (2013.01); *B32B 2437/00* (2013.01); *D10B 2501/06* (2013.01); *D10B 2503/06* (2013.01)

(58) Field of Classification Search
None
See application file for complete search history.

(56) References Cited

U.S. PATENT DOCUMENTS

2002/0142687 A1   10/2002   Tanabe et al.
2004/0011017 A1*  1/2004   Yuuki .............. D02G 3/04
                                                57/255

FOREIGN PATENT DOCUMENTS

CN   102864543 A   1/2013
CN   202898684 U   4/2013
(Continued)

OTHER PUBLICATIONS

Chattopadhyay, Design of Apparel Fabrics: Role of Fibre, Yarn and Fabric Parameters on its Funtional Attributes, Journal of Textile Engineering, vol. 54, No. 6, pp. 179-190, 2008.*

(Continued)

*Primary Examiner* — Shawn Mckinnon
(74) *Attorney, Agent, or Firm* — Oblon, McClelland, Maier & Neustadt, L.L.P.

(57) ABSTRACT

A gauze fabric includes a surface layer composed of twisted yarns, a back layer composed of twisted yarns, and a middle layer composed of twisted yarns. The middle layer is provided between the surface layer and the back layer. The surface layer and the back layer are directly and/or indirectly joined with each other. The twisted yarns in the surface layer are twisted yarns having twisting coefficient of 3.3 or less. The twisted yarns in the back layer are twisted yarns having twisting coefficient of 3.3 or less. The twisted yarns in the middle layer are twisted yarns having twisting coefficient of 3.5 or more. The gauze fabric has good touch feeling and is capable of being sewn.

12 Claims, 1 Drawing Sheet

(51) Int. Cl.
*B32B 5/06* (2006.01)
*B32B 5/26* (2006.01)
*B32B 5/02* (2006.01)
*A61F 13/00* (2006.01)
*D03D 15/00* (2006.01)

(56) References Cited

FOREIGN PATENT DOCUMENTS

| GB | 524191 | | 7/1940 |
|---|---|---|---|
| JP | 62-199837 | A | 9/1987 |
| JP | 11-323693 | A | 11/1999 |
| JP | H11323693 | * | 11/1999 |
| JP | 2004-091991 | A | 3/2004 |
| JP | 2004-107823 | A | 4/2004 |
| JP | 2004-107824 | A | 4/2004 |
| JP | 2004107824 | * | 4/2004 |
| JP | 2005-330613 | A | 12/2005 |
| JP | 2007-119941 | A | 5/2007 |
| JP | 2007-303008 | A | 11/2007 |
| JP | 2010-077542 | A | 4/2010 |
| JP | 3187096 | U | 10/2013 |
| JP | 3187096 | * | 11/2013 |
| JP | 3189066 | U | 2/2014 |
| WO | 2008/138589 | A2 | 11/2008 |

OTHER PUBLICATIONS

Neville, Arithmetical Calculations for Weaving Students, 2010, http://archive.org/stream/arithmeticalcalc00nevi/arithmeticalcalc00nevi_djvu.txt, page visted on Feb. 6, 2017.*
Machine translation of JP 2004107824, Tomita.*
Machine translation of JPH 11323693, Kamiwaki.*
Machine translation of JP3187096, 2013 (Year: 2013).*
International Search Report dated Feb. 18, 2014, in PCT/JP2013/084666, Filed Dec. 25, 2013.
Chinese Search Report dated Jul. 3, 2015 in CN 800192791, Filed Dec. 25, 2013.
Japanese Notice of Allowance dated Apr. 14, 2014 in JP 2014-510583 (with English translation).
Extended European Search Report issued in European Application No. 13900132.5 dated May 16, 2017.

* cited by examiner

GAUZE FABRIC

TECHNICAL FIELD

The present invention relates to a gauze fabric.

BACKGROUND ART

Gauze fabrics are a coarse-meshed plain woven fabric. For example, a cotton yarn (a single yarn of a yarn count of 40) is used for weaving the gauze fabrics. Exemplary patterns of the gauze fabrics include a single woven fabric, a double woven fabric, and a triple woven fabric. The single gauze fabric is employed, for example, for medical use and as a dishcloth. The double gauze fabric is employed for clothing, handkerchief, etc. The triple gauze fabric is employed for towels, bed and bedding, etc.

CITATION LIST

Patent Literature

[PATENT LITERATURE 1]
Japanese Unexamined Patent Application, First Publication No. 1999-323693
[PATENT LITERATURE 2]
Japanese Unexamined Patent Application, First Publication No. 2004-107823
[PATENT LITERATURE 3]
Japanese Unexamined Patent Application, First Publication No. 2004-107824
[PATENT LITERATURE 4]
Japanese Unexamined Patent Application, First Publication No. 2007-303008
[PATENT LITERATURE 5]
Japanese Utility Model Registration, First Publication No. 3187096

SUMMARY OF INVENTION

Technical Problem

Gauze is a coarse-meshed fabric, i.e., a loosely woven fabric. Because gauze is a coarse-meshed plain woven fabric, even when the gauze is woven into a multiple woven fabric, the resulting fabric will be still thin. Therefore, gauze is poor in bounce and softness. Especially gauze composed of twisted yarns is poor in bounce and softness. Because of its coarse-meshed structure, gauze is poor in heat-retaining property.

The present invention is made to solve the above problem. Namely, a purpose of the present invention is to provide a gauze fabric having a good touch feeling (a soft touch feeling) and breathability, further being excellent in heat-retaining property.

Solution to Problem

According to a first aspect of the present invention, proposed is a gauze fabric including
a surface layer composed of twisted yarns;
a back layer composed of twisted yarns; and
a middle layer composed of twisted yarns;
wherein the middle layer is provided between the surface layer and the back layer;
wherein the surface layer and the back layer are directly and/or indirectly joined with each other;
wherein the twisted yarns in the surface layer are twisted yarns having twisting coefficient of 3.3 or less;
wherein the twisted yarns in the back layer are twisted yarns having twisting coefficient of 3.3 or less; and
wherein the twisted yarns in the middle layer are twisted yarns having twisting coefficient of 3.5 or more.

According to a second aspect of the present invention, proposed is a gauze fabric including
a surface layer composed of twisted yarns;
a back layer composed of twisted yarns; and
a middle layer(s) composed of twisted yarns;
wherein the middle layer(s) is provided between the surface layer and the back layer;
wherein the surface layer and the back layer are directly and/or indirectly joined with each other;
wherein the twisted yarns in the surface layer are twisted yarns having twisting coefficient of 3.3 or less;
wherein the twisted yarns in the back layer are twisted yarns having twisting coefficient of 3.3 or less;
wherein the middle layer(s) is equal to or more than 1 layer; and
wherein the twisted yarns in at least one middle layer among the middle layer(s) are twisted yarns having twisting coefficient of 3.5 or more.

According to a third aspect of the present invention, proposed is the gauze fabric, wherein the surface layer and the back layer are joined together via the twisted yarns of the middle layer.

According to a fourth aspect of the present invention, proposed is the gauze fabric, wherein the twisted yarn, which twisting coefficient is equal to or more than 3.5, is a yarn made by twisting two or more yarns.

According to a fifth aspect of the present invention, proposed is the gauze fabric, wherein the twisted yarn which twisting coefficient is equal to or more than 3.5, is a double yarn.

According to a sixth aspect of the present invention, proposed is the gauze fabric, wherein the twisted yarn is selected from yarn count of 25 to yarn count of 80.

According to a seventh aspect of the present invention, proposed is the gauze fabric, wherein the gauze fabric is an N (N is an integer equal to or greater than 3) woven fabric.

According to a eighth aspect of the present invention, proposed is the gauze fabric, wherein the gauze fabric is a triple woven fabric.

According to an ninth aspect of the present invention, proposed is the gauze fabric, wherein the gauze fabric is a gauze fabric for garment.

According to a tenth aspect of the present invention, proposed is clothes manufactured with the gauze fabric.

According to a eleventh aspect of the present invention, proposed is bedding manufactured with the gauze fabric.

Advantageous Effect of Invention

Despite that the surface layer, the middle layer and the back layer are composed of twisted yarns, the gauze fabric of the present invention has a good touch feeling (a soft touch feeling) and breathability, further being excellent in heat-retaining property. Thus because the twisted yarns in the surface layer and the back layer are twisted yarns having twisting coefficient of 3.3 or less, the gauze fabric of the present invention has a good touch feeling (a soft touch feeling) and breathability, further being excellent in heat-retaining property.

Further, a shrinkage rate of the surface layer (back layer) differs from a shrinkage rate of the middle layer. As a result, the gauze fabric comes to have rich three-dimensional appearance (bulkiness). Even with the bulkiness, the gauze fabric is still light in weight. Further, such gauze fabric is excellent in heat-retaining property.

DESCRIPTION OF EMBODIMENTS

Figure 1:
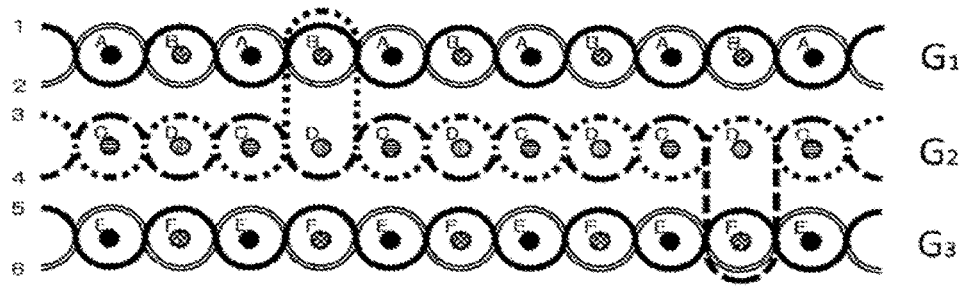
FIG. 1 is a cross-sectional view of a gauze fabric according to an embodiment of the present invention.

An embodiment of the present invention will be described below. A first invention is directed to a gauze fabric. The gauze fabric includes a surface, a back layer and a middle layer. The surface layer is composed by using twisted yarns. At least one layer of the middle layer(s) is composed by using twisted yarns. The back layer is composed by using twisted yarns.

The twisted yarns in the surface layer are twisted yarns having twisting coefficient of 3.3 or less. The twisted yarns in at least one layer of the middle layer(s) are twisted yarns having twisting coefficient of 3.5 or more. The twisted yarns in the back layer are twisted yarns having twisting coefficient of 3.3 or less.

The gauze fabric is used in various fields. Specifically, when the gauze fabric is used in a field of garment, the gauze fabric produces a large effect. For example, the gauze fabric is used as a material for clothes (e.g., gown, pajamas, and undershirt). As a matter of course, the use of gauze fabric is not limited to garments. For example, the gauze fabric is employed as a material for the use of various products for infants. For example, the gauze fabric is employed for the use of a material for bedding.

The gauze fabric is an N (N is an integer equal to or greater than 3) woven fabric. In the light of weight and cost, N is, preferably, 3, 4, or 5. More preferably, N is 3 (i.e., triple woven fabric). In the case of a triple woven fabric, the middle layer is one layer.

The gauze fabric includes a surface, a back layer and a middle layer. The middle layer(s), for example, are 1-3 layer(s). Preferably the middle layer is one layer.

The surface layer is composed by using twisted yarns. The twisted yarns in the surface layer are twisted yarns having twisting coefficient of 3.3 or less. The back layer is composed by using twisted yarns. The twisted yarns in the back layer are twisted yarns having twisting coefficient of 3.3 or less. Twisted yarn having twisting coefficient of 3.3 or less is non-twisted yarn. Thus, 0<twisting coefficient of twisted yarn 3.3. Preferably the twisting coefficient is 3.0 or less. Preferably, the twisting coefficient is 0.3 or more. More preferably, the twisting coefficient is 0.5 or more. Furthermore preferably, the twisting coefficient is 1.0 or more. At least one layer of the middle layer(s) is composed by using twisted yarns. The twisted yarns in the middle layer are twisted yarns having twisting coefficient of 3.5 or more. Preferably, the twisting coefficient is 3.8 or more. Especially preferably, the twisting coefficient is 4.0 or more. There is no particular upper limit. Some yarns without above features may be included in the gauze fabric so far as features of the present invention are not largely deteriorated. The number of twist of yarn deffers depending on yarn count (thickness). Strength of twist is represented by not number of twist but coefficient. For example, the number of twist per inch is equivalent to the value obtained by multiplying the square root of yarn count by coefficient. Yarn having twisting coefficient of 3.5-5.0 is commonly called as medium twisted yarn (ordinary yarn). Yarn having twisting coefficient of 5.0-8.0 is commonly called as hard twisted yarn. Yarn having twisting coefficient of 8.0 or more is commonly called as ultra-hard twisted yarn.

The surface layer and the back layer are directly and/or indirectly joined with each other. For example, the surface layer and the back layer are directly joined together via yarns. Alternatively, the surface layer and the middle layer are directly joined together via yarns (specifically, via twisted yarns composing the middle layer), and the back layer and the middle layer are directly joined together via yarns (specifically, via twisted yarns composing the middle layer). As a result, the surface layer and the back layer are indirectly joined together via the middle layer.

The twisted yarn having twisting coefficient of 3.5 or more is preferably a yarn which is made by twisting two or more yarns. Most preferable twisted yarn is a double yarn. Preferably, the twisted yarn is selected from yarn count of 25 to yarn count of 80 (more preferably, from yarn count of 40 to yarn count of 70). In a case where the twisted yarn is a double yarn, the twisted yarn is made of a combination of yarns selected from yarn count of 50 to yarn count of 160 (more preferably, from yarn count of 80 to yarn count of 140) and from yarn count of 50 to yarn count of 160 (more preferably, from yarn count of 80 to yarn count of 140).

The gauze fabric of the present embodiment has a soft touch feeling. More specifically, the surface layer and the back layer were composed of twisted yarns having twisting coefficient of 3.3 or less, and thus the resulting gauze fabric comes to have a soft touch feeling. The gauze fabric includes the surface layer (and the back layer) composed of twisted yarns having twisting coefficient of 3.3 or less and the middle layer composed of twisted yarns having twisting coefficient of 3.5 or more. Therefore, the resulting gauze is rich in three-dimensional appearance. This is because a shrinkage rate of the surface layer (back layer) differs from a shrinkage rate of the middle layer. Synergism of concave and convex structure (three-dimensional appearance) caused by the difference of the shrinkage rate, puffiness of yarns resulting from small twist, and puffiness of yarns resulting from unravelling of yarns increases a thickness of the material. As a result, the material comes to be soft and excellent in heat-retaining property. Further, the material is light in weight for its thickness. The gauze fabric of the present embodiment includes the surface layer, the back layer, and the middle layer which all are composed of twisted yarns and thus is rich in fabric strength. Therefore, this enables easiness of sewing of the gauze.

A second invention is directed to clothes (gown, pajamas, undershirt, etc.) or bedding (sheet, blanket, etc.). These products are manufactured with the above described gauze fabric.

More specific embodiment will be described below. However, the present invention is not limited to only the following embodiment. Various modifications and applications are also encompassed within the scope of the present invention in so far as features of the present invention are not largely deteriorated.

FIG. 1 is a cross sectional view of a gauze fabric (triple gauze fabric) according to a first embodiment of the present invention.

1 and 2 denote warps (warp yarns) composing a layer of gauze $G_1$ that is a first layer (surface layer/upper layer). A and B denote wefts (woof) composing the layer of gauze $G_1$ that is the first layer. The warps 1 and 2 and the wefts A and B all are twisted yarns. The first layer $G_1$ is composed of only twisted yarns. Twisting coefficient of twisted yarns is 3.0.

3 and 4 denote warps composing a layer of gauze $G_2$ that is a second layer (middle layer). C and D are wefts composing the layer of gauze $G_2$ that is the second layer. The warps 3 and 4 and the wefts C and D all are twisted yarns. The second layer $G_2$ is composed of only twisted yarns. Twisting coefficient of twisted yarns is 4.0. The twisted yarn is double yarn composed of two yarns of a yarn count of 120.

5 and 6 denote warps composing a layer of gauze $G_3$ that is a third layer (back layer/lower layer). E and F denote wefts composing the layer of gauze $G_3$ that is the third layer. The warps 5 and 6 and the wefts E and F all are twisted yarns. The third layer $G_3$ is composed of only twisted yarns. Twisting coefficient of twisted yarns is 3.0.

In a gauze fabric composed of the layers of gauze $G_1$, $G_2$, and $G_3$ which are laminated together, the warp 3 (or the warp 4) is entwined with the weft B (or the weft A) at adequate positions (locations) (see, FIG. 1). In other words, the twisted yarn (warp) 3 of the middle layer $G_2$ contributes to join the gauze $G_2$ as the second layer and the gauze $G_1$ as the first layer together.

In the gauze fabric composed of the layers of gauze $G_1$, $G_2$, and $G_3$ which are laminated together, the warp 4 (or the warp 3) is entwined with a weft F (or a weft E) at adequate positions (locations) (see, FIG. 1). In other words, the twisted yarn (warp) 4 of the middle layer $G_2$ contributes to join the gauze $G_2$ as the second layer and the gauze $G_3$ as the third layer together.

The gauze of the present embodiment includes layers which are joined together via the warps (wefts).

The gauze $G_1$ as the first layer, the gauze $G_2$ as the second layer, and the gauze $G_3$ as the third layer may be manufactured by a type of weave similar to a weave for manufacturing the conventional triple gauze fabric. As a matter of course, the type of weave is not limited thereto.

In the conventional N (N is an integer equal to or greater than 2) gauze fabric, a common type of warp was employed in each layer. To the contrary, in the N (N is an integer equal to or greater than 3) gauze fabric of the present invention, a twisted yarn having twisting coefficient of 3.3 or less is employed for the first layer (surface layer) and the Nth layer (back layer), and a twisted yarn having twisting coefficient of 3.5 or more is employed for at least one middle layer. Therefore, when manufacturing the N (N is an integer equal to or greater than 3) gauze fabric of the present invention, a device capable of supplying at least two different yarns was used.

A triple gauze fabric composed of the warps 1, 2, 3, 4, 5, and 6 and the wefts A, B, C, D, E, and F, the warps and the wefts being a twisted yarn (twisting coefficient of 3.0), was manufactured as a comparison example 1.

A triple gauze fabric composed of the warps 1, 2, 3, 4, 5, and 6 and the wefts A, B, C, D, E, and F, the warps and the wefts being a twisted yarn (twisting coefficient of 4.0), was manufactured as a comparison example 2.

A triple gauze fabric composed of the warps 1, 2, 5, and 6 and the wefts A, B, E, and F, the warps and the wefts being a twisted yarn (twisting coefficient of 4.0), and the warps 3 and 4 and the wefts C and D, the warps and the wefts being a twisted yarn (twisting coefficient of 3.0), was manufactured as a comparison example 3.

A triple gauze fabric composed of the warps 1, 2, 3, and 4 and the wefts A, B, C, and D, the warps and the wefts being a twisted yarn (twisting coefficient of 3.0), and the warps 5 and 6 and the wefts E and F, the warps and the wefts being a twisted yarn (twisting coefficient of 3.0), was manufactured as a comparison example 4.

A sewing ability was compared between the triple gauze fabric of the present embodiment and each of the triple gauze fabrics of the comparison examples 1, 2, 3, and 4. As a result, sewing condition was not good in the triple gauze fabric of the comparison example 1. Only with a small tensile force being applied, garments (clothes) manufactured with the triple gauze fabric of the comparison example 1 were torn in their sewing areas. To the contrary, sewing condition was good in the triple gauze fabric of the present embodiment. More specifically, garments (clothes) manufactured with the triple gauze fabric of the present embodiment were not torn in their sewing areas. Sewing condition was good in each of the triple gauze fabrics of the comparison examples 2, 3, and 4.

A feel of touch was compared between the triple gauze fabric of the present embodiment and each of the triple gauze fabrics of the comparison examples 1, 2, 3, and 4. As a result, the triple gauze fabric (in which twisted yarns having twisting coefficient of 3.0 were substantially employed for all the warps and wefts of the surface layer and for all the warps and wefts of the back layer) of the present embodiment was excellent in feel of touch. To the contrary, the triple gauze fabrics of the comparison examples 2, 3, and 4 were degraded in feel of touch and softness in comparison with the triple gauze fabric of the present invention. Only little portions of the twisted yarns 3 and 4 are exposed to the surface (see, FIG. 1). A rate of exposure of the twisted yarns 3 and 4, however, is almost 0. Therefore, the feel of touch is not bad.

Further, in the triple gauze fabric of the present embodiment, the surface layer (back layer) was composed of twisted yarns having twisting coefficient of 3.0, and the middle layer was composed of twisted yarns having twisting coefficient of 4.0. This made the triple gauze fabric of the present embodiment rich in three-dimensional appearance. This rich in three-dimensional appearance brought about excellent heat-retaining property, softness, and light in weight for its thickness.

Hereinabove, a description was made with respect to the triple gauze fabric. The present invention, however, may be an N (N is an integer equal to or greater than 4) gauze fabric. In this case, the surface layer and the back layer are woven with twisted yarns having twisting coefficient of 3.3 or less, and at least one middle layer is woven with twisted yarns having twisting coefficient of 3.5 or more. Alternatively, all the middle layers may be woven with twisted yarns having twisting coefficient of 3.5 or more. In a case where the fabric includes two or more middle layers, it is sufficient that at least one middle layer is woven with twisted yarns having twisting coefficient of 3.5 or more. However, in a case where the N (N is an integer equal to or greater than 4) gauze fabric including two or more middle layers is compared to the triple gauze fabric, the triple gauze fabric is more excellent in lightness and cost.

Figure 2:
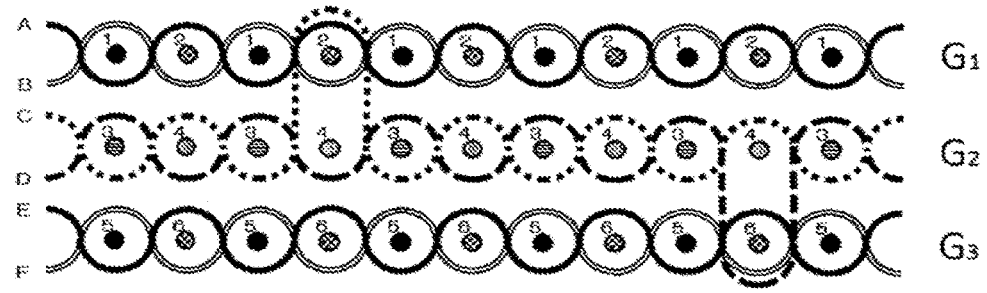
FIG. 2 is a cross-sectional view of a gauze fabric according to another embodiment of the present invention.

FIG. 1 is a cross sectional view of the gauze fabric including layers which are joined together via the warps (warp yarns). FIG. 2 is a cross sectional view of the gauze fabric including layers which are joined together via the wefts (woof). The gauze fabric of FIG. 1 differs from the gauze fabric of FIG. 2 only in whether warps are employed for joining or wefts are employed for joining. Structures of the gauze fabric of FIG. 1 and the gauze fabric of FIG. 2 are identical to each other except for the above described joining structure. Therefore, a detailed description thereof is omitted here. The joining may be performed via both of warps and wefts.

In an example of the gauze fabric of FIG. 1, the gauze $G_2$ and the gauze $G_1$ are joined with each other, and the gauze $G_2$ and the gauze $G_3$ are joined with each other. However, such a structure may be also employed that the surface layer $G_1$ and the back layer $G_3$ are directly joined with each other, and thereby the middle layer $G_2$ between the surface layer $G_1$ and the back layer $G_3$ is indirectly joined with them.

In FIG. 1 and FIG. 2, the thickness of warps and the thickness of wefts may look different from each other. However, in the above described embodiment, thicknesses of warps and wefts are substantially the same. As a matter of course, the thicknesses may differ from one another.

REFERENCE CHARACTER LIST $G_1$ first layer (surface layer)
$G_2$ second layer (middle layer)
$G_3$ third layer (back layer)
1, 2, 5, 6 warp (twisted yarn: twisting coefficient of 3.3 or less)
A, B, E, F weft (twisted yarn: twisting coefficient of 3.3 or less)
3, 4 warp (twisted yarn: twisting coefficient of 3.5 or more)
C, D weft (twisted yarn: twisting coefficient of 3.5 or more)

The invention claimed is:

1. A gauze fabric comprising:
a surface layer composed of twisted yarns;
a back layer composed of twisted yarns; and
a middle layer composed of twisted yarns;
wherein the middle layer is provided between the surface layer and the back layer;
wherein the surface layer and the back layer are directly and/or indirectly joined with each other;
wherein the twisted yarns in the surface layer are twisted yarns that shrink less than the middle layer and have a twisting coefficient of 3.3 or less;
wherein the twisted yarns in the back layer are twisted yarns that shrink less than the middle layer and have a twisting coefficient of 3.3 or less; and
wherein the twisted yarns in the middle layer are twisted yarns that shrink more than the surface layer and the back layer to form a concave and convex structure, and have a twisting coefficient of 3.5 or more,
wherein a difference between the twisting coefficient of the surface layer and the middle layer is greater than or equal to 0.3 and less than or equal to 3.0, and
wherein a difference between the twisting coefficient of the back layer and the middle layer is greater than or equal to 0.3 and less than or equal to 3.0.

2. The gauze fabric according to claim 1,
wherein the middle layer is at least one middle layer;
wherein the at least one middle layer is composed of twisted yarns which twisting coefficient is equal to or more than 3.5.

3. The gauze fabric according to claim 1, wherein the surface layer and the back layer are joined together via the twisted yarns composing the middle layer.

4. The gauze fabric according to claim 1, wherein the twisted yarn, which twisting coefficient is equal to or more than 3.5, is a yarn made by twisting two or more yarns.

5. The gauze fabric according to claim 1, wherein the twisted yarn, which twisting coefficient is equal to or more than 3.5, is a double yarn.

6. The gauze fabric according to claim 1, wherein the twisted yarn, which twisting coefficient is equal to or more than 3.5, is selected from yarn count of 25 to yarn count of 80.

7. The gauze fabric according to claim 1, wherein the gauze fabric is an N (N is an integer equal to or greater than 3) woven fabric.

8. The gauze fabric according to claim 7, wherein the gauze fabric is a triple woven fabric.

9. The gauze fabric according to claim 1, wherein the gauze fabric is a gauze fabric for garment.

10. Clothes manufactured with the gauze fabric according to claim 1.

11. Bedding manufactured with the gauze fabric according to claim 1.

12. The gauze fabric according to claim 1, wherein a difference between the twisting coefficient of the surface layer and the middle layer is greater than or equal to 0.8, and
wherein a difference between the twisting coefficient of the back layer and the middle layer is greater than or equal to 0.8.

* * * * *